(12) United States Patent
Qian

(10) Patent No.: US 10,995,082 B2
(45) Date of Patent: May 4, 2021

(54) CATIONIC PHOTOINITIATOR AND PREPARATION METHOD AND USE THEREOF

(71) Applicants: Changzhou Tronly New Electronic Materials Co., Ltd., Jiangsu (CN); Changzhou Tronly Advanced Electronic Materials Co., Ltd., Jiangsu (CN)

(72) Inventor: Xiaochun Qian, Changzhou (CN)

(73) Assignees: Changzhou Tronly New Electronic Materials Co., Ltd., Jiangsu (CN); Changzhou Tronly Advanced Electronic Materials Co., Ltd., Jiangsu (CN)

(*) Notice: Subject to any disclaimer, the term of this patent is extended or adjusted under 35 U.S.C. 154(b) by 0 days.

(21) Appl. No.: 16/318,890

(22) PCT Filed: Aug. 1, 2017

(86) PCT No.: PCT/CN2017/095371
§ 371 (c)(1),
(2) Date: Jan. 18, 2019

(87) PCT Pub. No.: WO2018/028461
PCT Pub. Date: Feb. 15, 2018

(65) Prior Publication Data
US 2019/0218199 A1    Jul. 18, 2019

(30) Foreign Application Priority Data
Aug. 8, 2016 (CN) .......................... 201610646348.7

(51) Int. Cl.
| C08K 5/36 | (2006.01) |
| C07D 335/16 | (2006.01) |
| C07D 333/76 | (2006.01) |
| C07C 381/12 | (2006.01) |
| C08F 2/50 | (2006.01) |
| G03F 7/004 | (2006.01) |
| C08G 59/68 | (2006.01) |
| C09K 3/00 | (2006.01) |
| C07D 327/08 | (2006.01) |

(52) U.S. Cl.
CPC .......... *C07D 335/16* (2013.01); *C07C 381/12* (2013.01); *C07D 327/08* (2013.01); *C07D 333/76* (2013.01); *C08F 2/50* (2013.01); *C08G 59/68* (2013.01); *C08K 5/36* (2013.01); *C09K 3/00* (2013.01); *G03F 7/004* (2013.01)

(58) Field of Classification Search
CPC .................................. G03F 7/00; C08K 5/36
See application file for complete search history.

(56) References Cited

U.S. PATENT DOCUMENTS

| 8,192,590 | B1* | 6/2012 | Belfield ................. C07B 45/00 |
| | | | 204/157.7 |
| 2005/0176969 | A1 | 8/2005 | Herlihy et al. |
| 2009/0197987 | A1 | 8/2009 | Hayoz et al. |
| 2009/0208872 | A1 | 8/2009 | Wolf et al. |
| 2010/0087563 | A1 | 4/2010 | Hayoz et al. |
| 2010/0297541 | A1 | 11/2010 | Hayoz et al. |
| 2010/0297542 | A1 | 11/2010 | Hayoz et al. |
| 2011/0152540 | A1 | 6/2011 | Nakayashiki et al. |
| 2011/0300482 | A1 | 12/2011 | Suzuki et al. |
| 2020/0048191 | A1 | 2/2020 | Suga et al. |

FOREIGN PATENT DOCUMENTS

| CN | 1989145 A | 6/2007 |
| CN | 101778818 A | 7/2010 |
| CN | 104267578 A | 1/2015 |
| CN | 104781304 A | 7/2015 |
| CN | 105130860 A | 12/2015 |
| EP | 2 186 799 A1 | 5/2010 |
| JP | 2011-32263 A | 2/2011 |
| JP | 2012-167051 A | 9/2012 |
| JP | 2013-234320 A | 11/2013 |
| JP | 2014-70020 A | 4/2014 |
| WO | 03/002557 A1 | 1/2003 |

(Continued)

OTHER PUBLICATIONS

Yanez, C.O., et al. "Characterization of novel sulfonium photoacid generators and their microwave-assisted synthesis." Chem. Commun. (2009), pp. 827-829. (Year: 2009).*

(Continued)

*Primary Examiner* — John S Kenyon
(74) *Attorney, Agent, or Firm* — Seed IP Law Group LLP

(57) ABSTRACT

This invention discloses a novel cationic photoinitiator and a preparation method and use thereof. The cationic photoinitiator has a structure as represented by general formula (I) below. It can match a longer absorption wavelength in the process of application and has an outstanding photosensitive property, and has characteristics of no proneness to migration and good yellowing resistance.

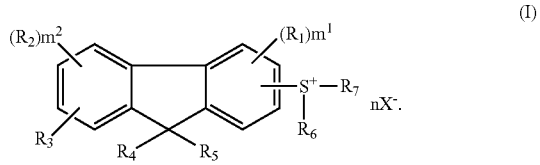

13 Claims, No Drawings

(56) References Cited

FOREIGN PATENT DOCUMENTS

| WO | 03/072567 A1 | 9/2003 | |
|---|---|---|---|
| WO | WO-03072567 A1 * | 9/2003 | ........... C07D 333/76 |
| WO | 2009/020089 A1 | 2/2009 | |
| WO | 2010/095385 A | 8/2010 | |
| WO | 2017/212963 A1 | 12/2017 | |
| WO | 2018/020974 A1 | 2/2018 | |
| WO | 2018/074382 A1 | 4/2018 | |

OTHER PUBLICATIONS

Japanese Office Action, for Japanese Patent Application No. 2019-501977, dated Jan. 6, 2020, 8 pages (with English Machine Translation).

Supplementary European Search Report, for European Patent Application No. 17838591.0, dated Jan. 21, 2020, 8 pages.

Yanez et al., "Characterization of novel sulfonium photoacid generators and their microwave-assisted synthesis," *Chem. Commun* :827-829, 2009.

* cited by examiner

CATIONIC PHOTOINITIATOR AND PREPARATION METHOD AND USE THEREOF

TECHNICAL FIELD

This invention belongs to the technical field of organic photocuring, and particularly to a novel cationic photoinitiator and a preparation method and use thereof.

BACKGROUND ART

A photoinitiator is a key component of a photocurable product and has a dominating effect on the cure rate of the photocurable product. According to different mechanisms of initiation, photoinitiators may be divided into cationic photoinitiators and radical photoinitiators. Compared to radical polymerization, a cationic photocuring system has the advantages of small polymerization inhibition by oxygen, small volume shrinkage upon curing, and wide selection of types of resins. In China, researches and developments of cationic photocuring systems fall behind, and there are few companies capable of performing industrial production.

Triarylsulfonium salts are a type of cationic photoinitiators, which are the most widely used at present and have good properties. They are superior to diaryliodonium salts in terms of absorption wavelength, thermal stability, initiation activity, and the like. However, the maximal absorption wavelength of this type of photoinitiators is still less than 300 nm, so that long-wavelength light sources cannot be effectively utilized and there are problems with solubility and mobility, which limit the use to some extent. Improvements in their structures have been tried, such as introduction of long-chain alkyl groups to improve their solubilities, introduction of multifunctional groups to improve their initiation efficiency and thermal stability, and the like. However, in practical use, there are deficiencies such as generation of micromolecular compounds due to low migration resistance, low yellowing resistance, and the like with respect to these improved structures, and initiation efficiency is still desired to be further improved. To this end, the title photoinitiator is developed.

SUMMARY OF THE INVENTION

With respect to the deficiencies in the prior art, an object of this invention is first to provide a novel cationic photoinitiator. It has been found in studies that the photoinitiator obtained by incorporating a sulfonium salt structure and a fluorene structure as described below has a red shift of absorption wavelength and an outstanding photosensitive property, and has characteristics of no proneness to and good yellowing resistance.

In order to achieve the technical effect described above, a technical solution used in this invention is as follows.

A cationic photoinitiator, which has a structure as represented by general formula (I):

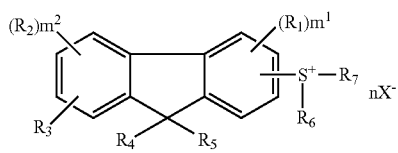
(I)

wherein,
$R_1$ and $R_2$ each independently represent a halogen, OH, CN, $NO_2$, a $C_1$-$C_{20}$ linear or branched alkyl group, a $C_3$-$C_{20}$ cycloalkyl group, a $C_4$-$C_{20}$ cycloalkylalkyl group, a $C_4$-$C_{20}$ alkylcycloalkyl group, or a $C_6$-$C_{40}$ aryl or heteroaryl group, wherein —$CH_2$— may be optionally substituted with —O—, —S—, —NH—, —CO—, —COO—, or —OCO—;

$m^1$ and $m^2$ represent numbers of $R_1$ and $R_2$ respectively, and are each independently selected from integers of 0-3;

$R_4$ and $R_5$ each independently represent hydrogen, a $C_1$-$C_{10}$ linear or branched alkyl group, a $C_3$-$C_{10}$ cycloalkyl group, a $C_4$-$C_{12}$ cycloalkylalkyl group, or a $C_4$-$C_{12}$ alkylcycloalkyl group, wherein —$CH_2$— may be optionally substituted with —O—, —S—, —CO—, —COO—, or —OCO—; and optionally, $R_4$ and $R_5$ may be linked to form a ring;

$R_6$ and $R_7$ may be the same or may be different, and each independently represent a phenyl group, a diphenyl sulfide group, a benzophenone group, a fluorenyl group, a diphenyl ether group, or a carbazolyl group, wherein hydrogen may be optionally substituted with a halogen, CN, $NO_2$, or a $C_1$-$C_5$ alkyl group, and —$CH_2$— in the $C_1$-$C_8$ alkyl group may be optionally substituted with —O—, —S—, —CO—, —COO—, or —OCO—; optionally, $R_6$ and $R_7$ may be linked to form a ring;

$R_3$ represents hydrogen, a halogen, CN, $NO_2$, $R_8$, —CO—$R_8$, or a $S(R_6)(R_7)$ group; RR represents a $C_1$-$C_{10}$ linear or branched alkyl group, a $C_3$-$C_{10}$ cycloalkyl group, a $C_4$-$C_{15}$ cycloalkylalkyl group, a $C_6$-$C_{20}$ aryl group, or a $C_7$-$C_{20}$ arylalkyl group, wherein in the cycloalkyl structure and the aryl structure, H may be optionally substituted with a $C_1$-$C_6$ alkyl group, and —$CH_2$— may be optionally substituted with —O—, —S—, —NH—, —CO—, —COO—, or —OCO—;

$X^-$ represents a non-nucleophilic anion; and
n is 1 or 2.

As a preferable technical solution, in the cationic photoinitiator represented by general formula (I) described above, $R_1$ and $R_2$ each independently represent a halogen, OH, CN, $NO_2$, a $C_1$-$C_{10}$ linear or branched alkyl group, a $C_3$-$C_{10}$ cycloalkyl group, a $C_4$-$C_{12}$ cycloalkylalkyl group, a $C_4$-$C_{12}$ alkylcycloalkyl group, or a $C_6$-$C_{20}$ aryl or heteroaryl group, wherein —$CH_2$— may be optionally substituted with —O—, —S—, —NH—, —CO—, —COO—, or —OCO—.

Preferably, $m^1$ and $m^2$ are each independently selected from integers of 0-2. Further preferably, both $m^1$ and $m^2$ are 0.

Preferably, $R_4$ and $R_5$ each independently represent hydrogen, a $C_1$-$C_8$ linear or branched alkyl group, a $C_3$-$C_6$ cycloalkyl group, or a $C_4$-$C_{10}$ cycloalkylalkyl group, wherein acyclic —$CH_2$— may be optionally substituted with —O—, —S—, —CO—, —COO—, or —OCO—; and optionally, $R_3$ and $R_4$ may be linked to each other to form a cycloalkyl group.

Preferably, $R_6$ and $R_7$ each independently represent a phenyl group, a diphenyl sulfide group, a benzophenone group, a fluorenyl group, a diphenyl ether group, or a carbazolyl group, wherein hydrogen may be optionally substituted with CN, $NO_2$, or a $C_1$-$C_4$ alkyl group, and —$CH_2$— in the $C_1$-$C_4$ alkyl group may be optionally substituted with —O—, —S—, —CO—, —COO—, or —OCO—.

Further preferably, $R_6$ and $R_7$ are each independently selected from the following groups:

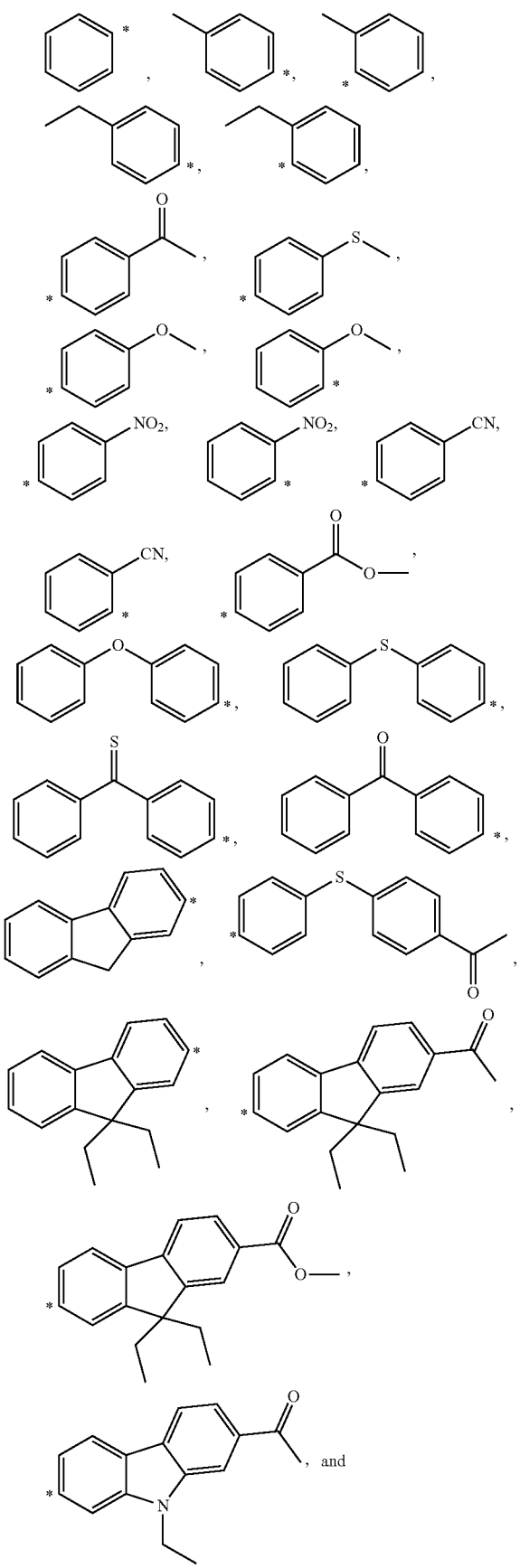

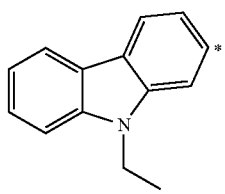

$R_6$ and $R_7$ may also be linked to each other to form a ring via a sulfide ion; and preferably forms the following groups:

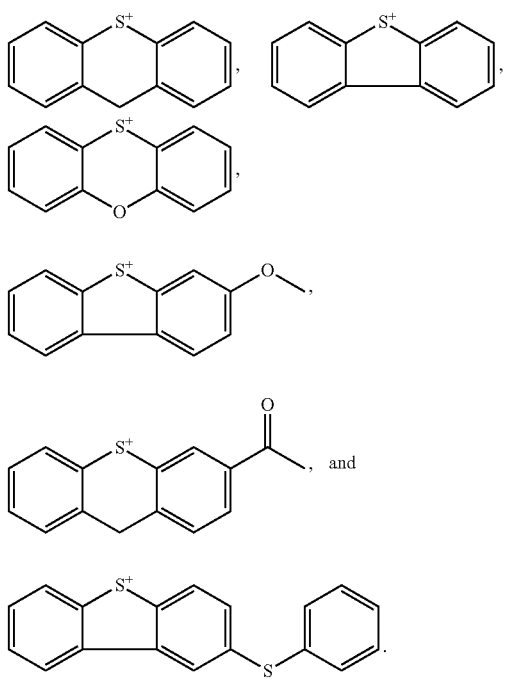

Preferably, $R_3$ represents hydrogen, a halogen, CN, $NO_2$, $R_8$, —CO—$R_8$, or a $S(R_6)(R_7)$ group; $R_8$ represents a $C_1$-$C_6$ linear or branched alkyl group, a $C_3$-$C_8$ cycloalkyl group, a $C_4$-$C_{10}$ cycloalkylalkyl group, a $C_6$-$C_{10}$ aryl group, or a $C_7$-$C_{12}$ arylalkyl group, wherein in the cycloalkyl structure and the aryl structure, H may be optionally substituted with a $C_1$-$C_4$ alkyl group, and acyclic —$CH_2$— may be optionally substituted with —O—, —S—, —NH—, —CO—, —COO—, or —OCO—.

Further preferably, when $R_3$ represents a $S^+(R_6)(R_7)$ group, it is bilaterally symmetrical with a $S^+(R_6)(R_7)$ group on the other side.

Preferably, $X^-$ is selected from $C_mF_{2m+1}SO_3^-$, $BF_4^-$, $SbF_6^-$, $AsF_6^-$, $PF_6^-$, and $B(C_6Q_5)_4^-$, wherein Q represents hydrogen or a halogen, and m is an integer of 1-8. Further preferably, $X^-$ is selected from $CF_3SO_3^-$, $C_4F_9SO_3^-$, $C_8F_{17}SO_3^-$, $PF_6^-$, $AsF_6^-$, $SbF_6^-$, or $B(C_6H_5)_4^-$, $B(C_6F_5)_4^-$.

The value of n is the same as the number of $S^+(R_6)(R_7)$ groups in the general formula (I). When $R_3$ represents a $S^+(R_6)(R_7)$ group, n is 2; and when $R_3$ does not represent a $S^+(R_6)(R_7)$ group, n is 1.

Without limitation, the cationic photoinitiator of this invention may be selected from the following structures:

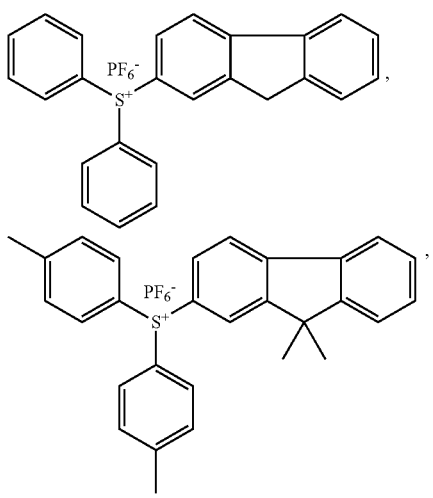
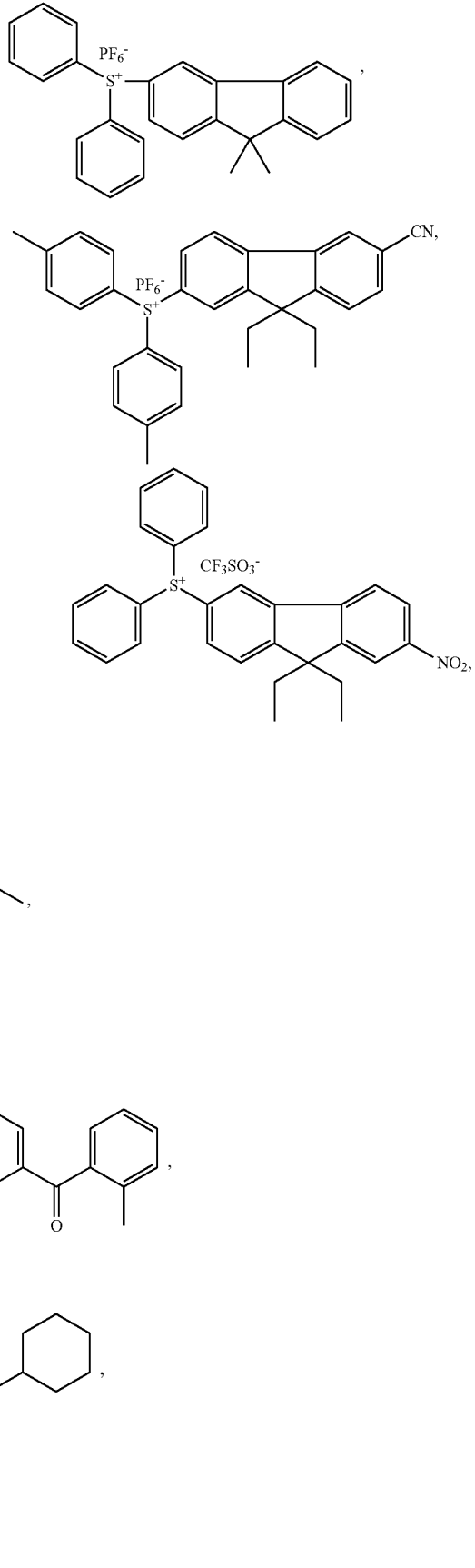

-continued
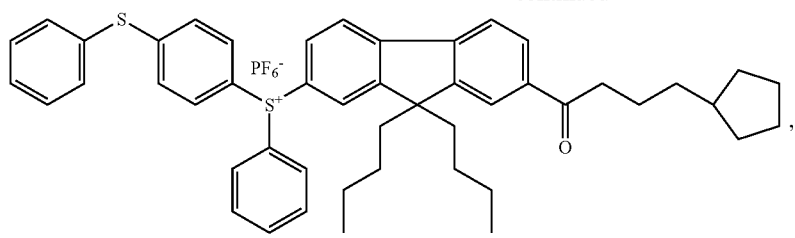,
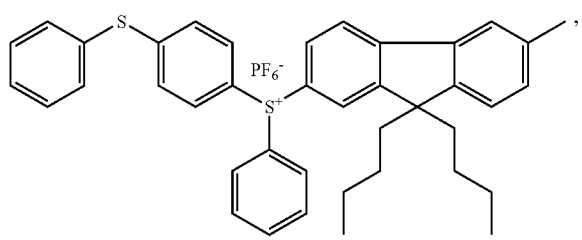,
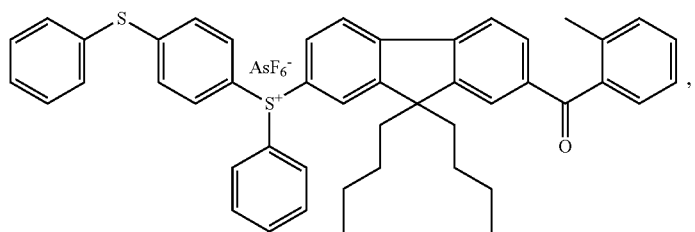,
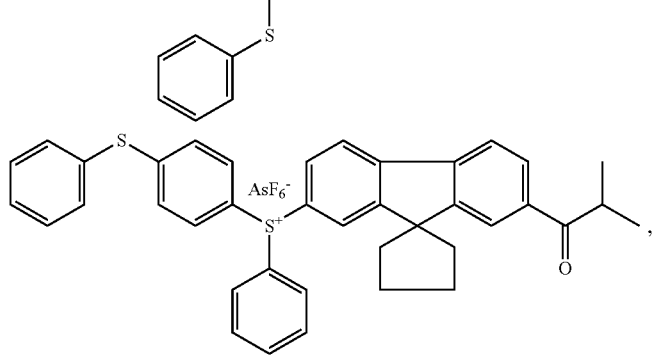,
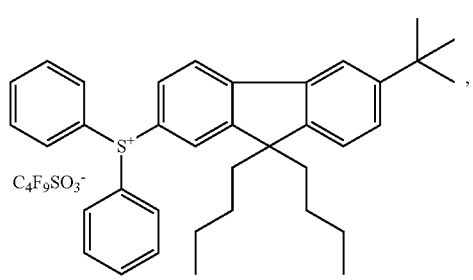, 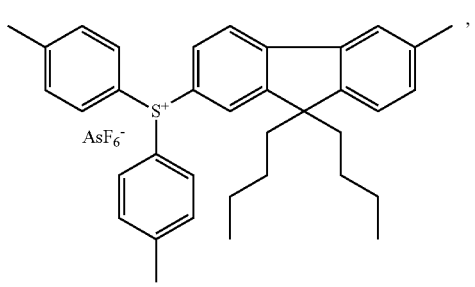,
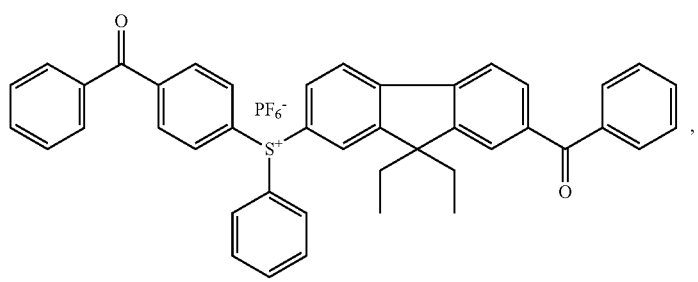, -continued
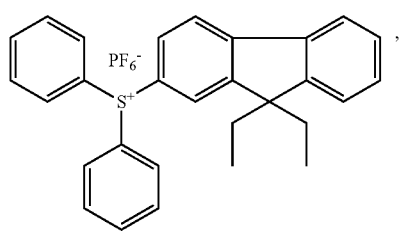
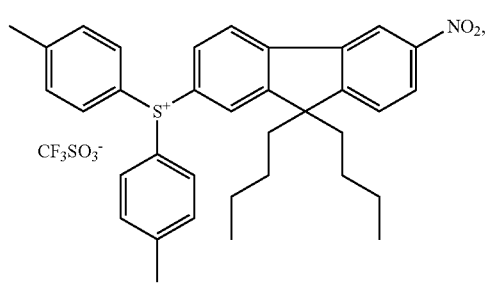
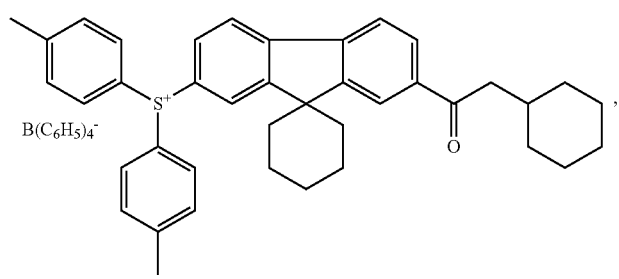
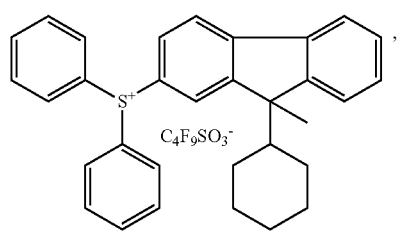
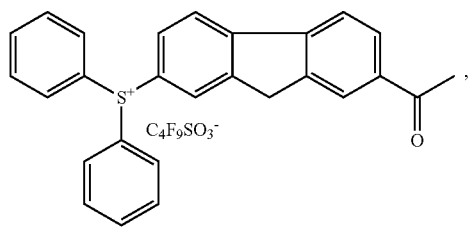
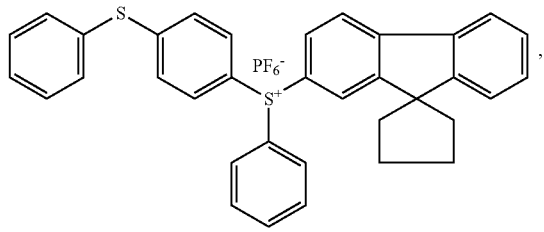
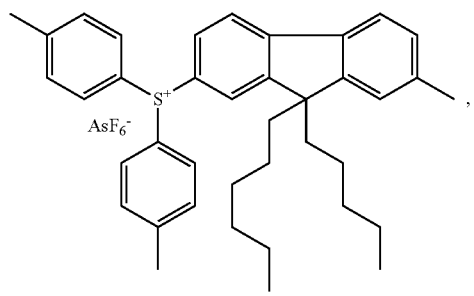
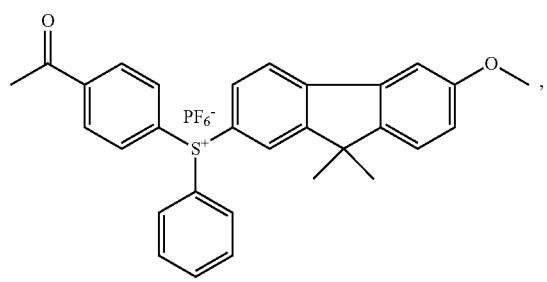
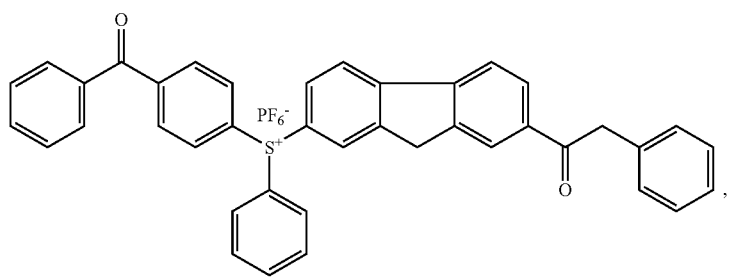

-continued
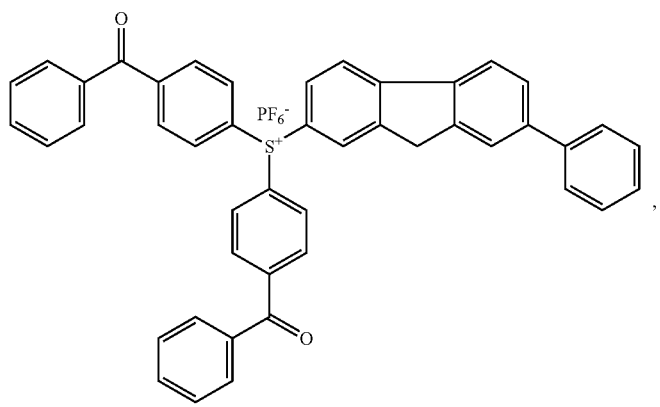
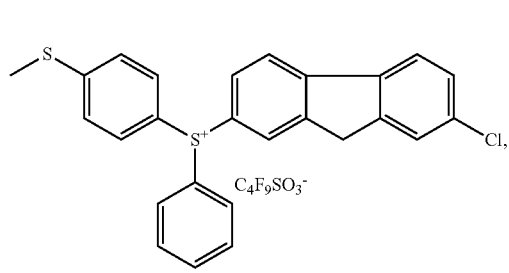
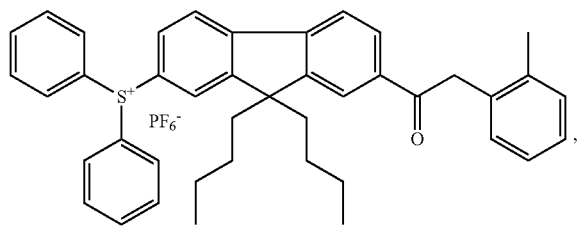
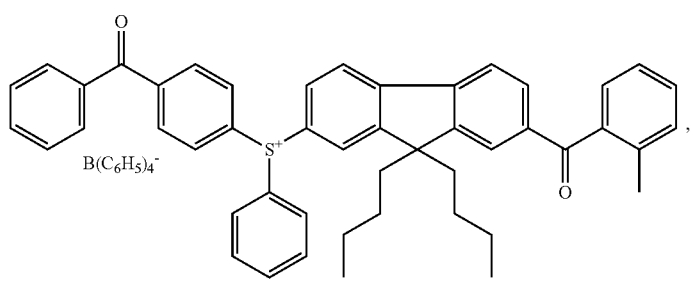
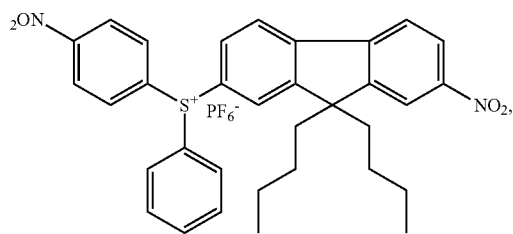
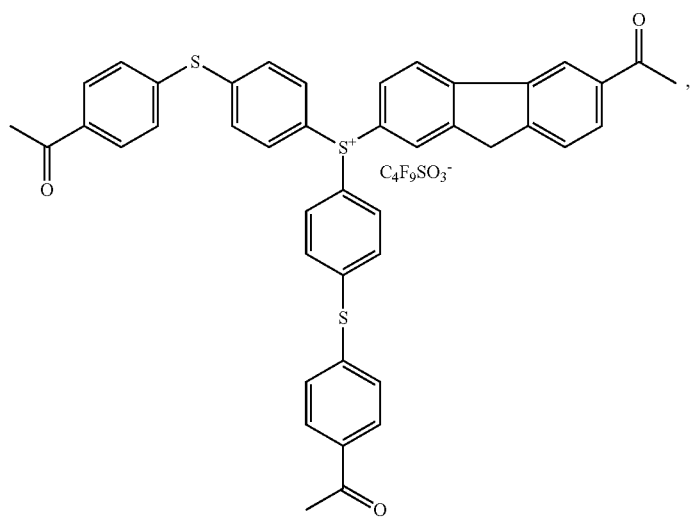

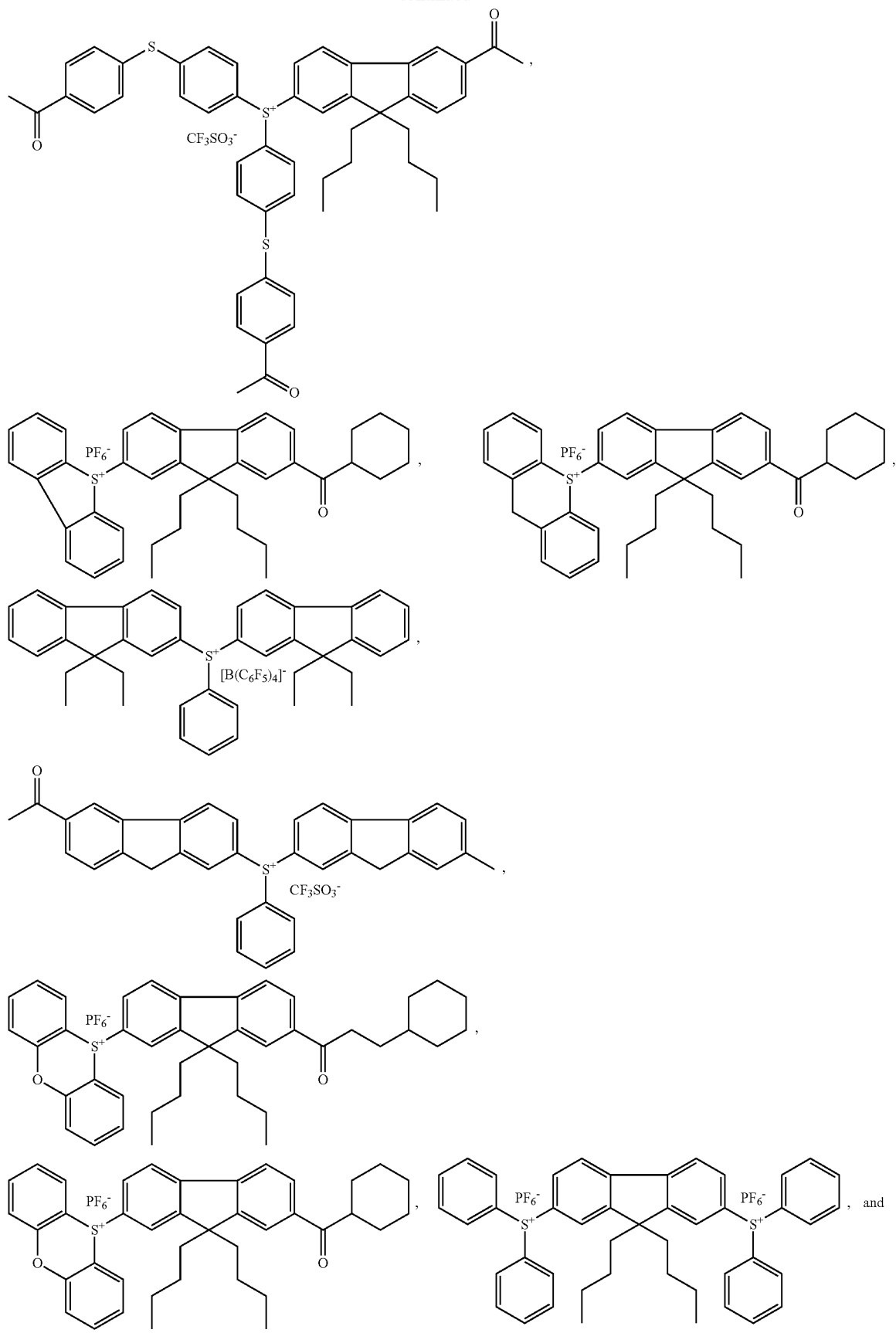

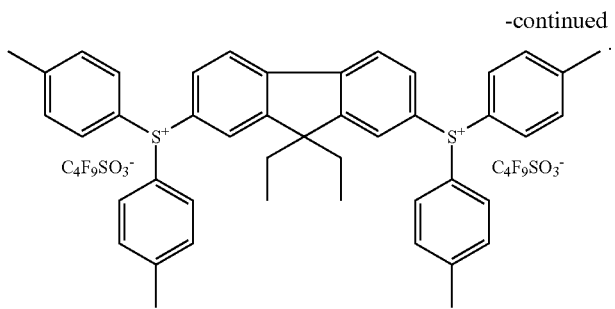

This invention also relates to a preparation method of the novel cationic photoinitiator represented by the general formula (I) described above, and the reaction process flow thereof is as shown below:

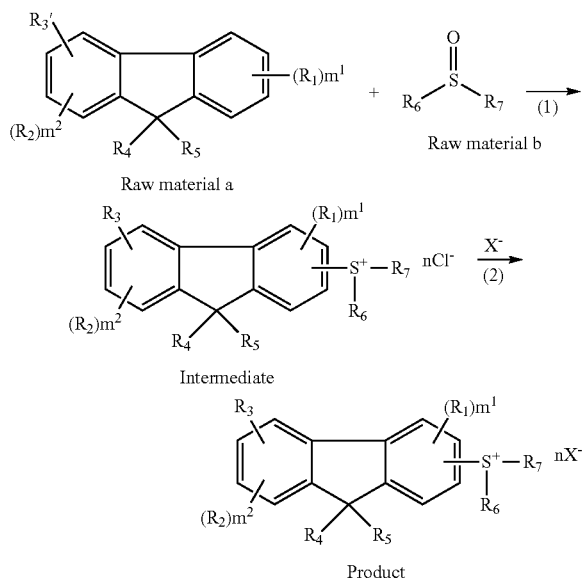

wherein $R_3'$ represents hydrogen when $R_3$ represents a $S^+(R_6)(R_7)$ group, and $R_3'=R_3$ in other cases;

it specifically comprises the steps of:

(1) synthesis of the intermediate, wherein the raw material a and the raw material b are subjected to Friedel-Crafts reaction in an organic solvent under the action of aluminum trichloride or zinc chloride to synthesize the intermediate:

(2) synthesis of the product, wherein the intermediate is added to an organic solvent in which NaX or KX is dissolved and dissolved with stirring, deionized water is subsequently added with stirring to precipitate a solid, and suction filtration and recrystallization are performed to obtain the product; wherein X in NaX and KX is the non-nucleophilic anion described above.

All of the raw materials used in the preparation method described above are compounds which are known in the prior art, commercially available, or conveniently prepared by known synthetic methods. Here, the raw material a may be synthesized with reference to methods disclosed in Patents such as Chinese Patent Application Nos. 201010557275.7, 200910030326.8, 2015109373280.0, and the like, which are incorporated hereby for reference in their entireties.

Reactions involved in steps (1) and (2) are all conventional reactions for synthesizing similar compounds in the art. On the basis of knowing the idea of synthesis disclosed in this invention, specific reaction conditions will be easily determined for a person skilled in the art.

In the Friedel-Crafts reaction in step (1), the reaction temperature is typically −10-30° C. The organic solvent used is not specially limited, as long as it can dissolve raw materials and has no adverse influence on the reaction, such as dichloromethane, dichloroethane, benzene, toluene, xylene, and the like.

The ion exchange reaction in step (2) is performed in a solvent system. The organic solvent used is not specially limited, as long as it can dissolve the raw materials of the reaction, can be miscible with water, and has no adverse influence on the reaction, such as acetone, methyl ethyl ketone, methyl isobutyl ketone, cyclohexanone, methanol, ethanol, and isopropanol. The reaction temperature is not particularly limited, and room temperature is appropriate.

The present invention also includes use of the cationic photoinitiator represented by the general formula (I) described above in photocurable composition. The cationic photoinitiator or mixtures thereof may be directly used in a formulation, or may be used in combination with other cationic photoinitiators. In use, a well-known additive, such as a solvent, a sensitizer, a pigment, a filler, a defoaming agent, a leveling agent, a non-reactive resin, and the like, may also be optionally added to a photocurable composition containing the cationic photoinitiator of this invention as needed. Without limitation, the photoinitiator of this invention may be used in aspects such as a paint, a coating agent, a photoresist, a photosensitive material, a sealing material, an ink, an adhesive, a polarizing film, an epoxy floor, and the like. The photoinitiator can match a longer absorption wavelength in the process of application, and provides properties such as excellent solubility, low mobility, and good yellowing resistance.

DESCRIPTION OF EMBODIMENTS

Hereafter, this invention will be further illustrated in conjunction with specific Examples, but it is not to be understood that the scope of this invention is limited thereto.

PREPARATION EXAMPLE

Example 1

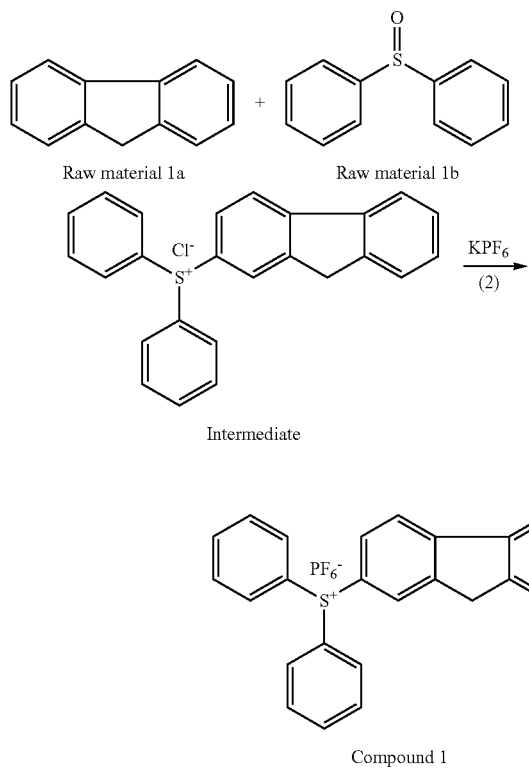

(1) Preparation of intermediate 1a 83 g of a raw material 1a, 67 g of aluminum trichloride, and 200 mL of dichloromethane were added to a 1000 mL four-neck flask, and the temperature was reduced to 0° C. by an ice water bath. 101 g of a raw material 1b was dissolved in 200 mL of dichloromethane to form a mixed solution. The mixed solution was subsequently charged into a dropping funnel, and the temperature was controlled at 10° C. or less. This mixed solution was dropped into the four-neck flask within about 2 h. Stirring was continued for 24 h after completion of dropping, and liquid phase tracking was performed until the concentration of the raw materials did not change any longer. The materials were then slowly poured into 800 g of deionized water with stirring to precipitate a solid, and suction filtration was performed to obtain a light yellow solid. This light yellow solid was dried in an oven at 80° C. for 2 h to obtain 152 g of the intermediate 1a with a yield of 79% and a purity of 98%.

(2) Preparation of compound 1

152 g of potassium hexafluorophosphate was dissolved in 150 mL of acetone, and 115 g of the intermediate 1a prepared in step (1) was then added. Stirring was performed at normal temperature until the intermediate 1a was dissolved. 300 mL of deionized water was then added to precipitate a white solid, suction filtration and recrystallization with methanol were performed to obtain 196 g of a solid. The solid was dried at 70° C. for 5 h to obtain the compound 1 with a yield of 92% and a purity of 98%.

The structure of the product was confirmed by MS and $^1$H-NMR.

MS(m/z): 352 (M+1)$^+$;

$^1$H-NMR (CDCl$_3$, 500 MHz): 3.9013 (2H, s), 7.3611-7.7658 (18H, m).

Example 2

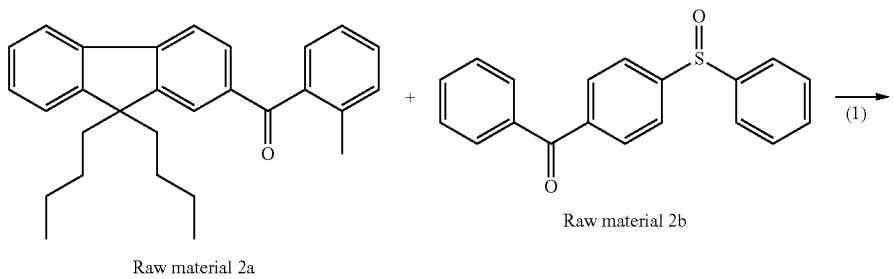

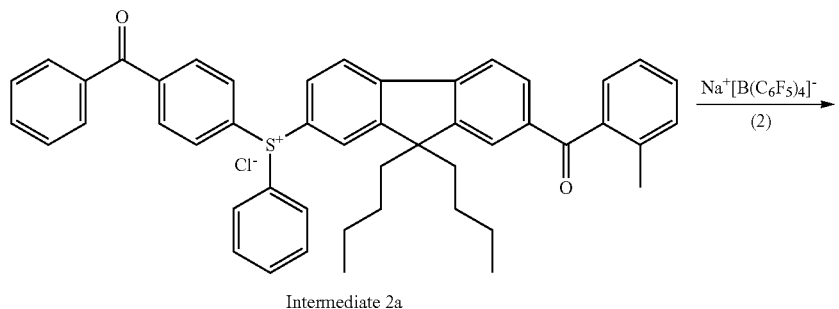

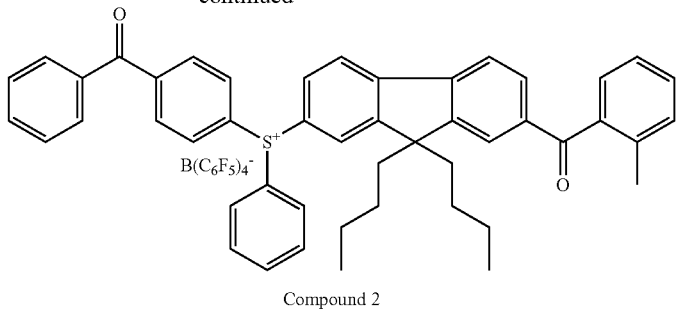

Compound 2

(1) Preparation of Intermediate 2a 40 g of a raw material 2a, 14 g of aluminum trichloride, and 50 mL of dichloromethane were added to a 500 mL four-neck flask, and the temperature was reduced to 0° C. by an ice water bath. 31 g of a raw material 2b was dissolved in 50 mL of dichloromethane to form a mixed solution. The mixed solution was subsequently charged into a dropping funnel, and the temperature was controlled at 10° C. or less. This mixed solution was dropped into the four-neck flask within about 2 h. Stirring was continued for 24 h after completion of dropping, and liquid phase tracking was performed until the concentration of the raw materials did not change any longer. The materials were then slowly poured into 200 g of deionized water with stirring to precipitate a solid, and suction filtration was performed to obtain a light yellow solid. This light yellow solid was dried in an oven at 80° C. for 2 h to obtain 46 g of the intermediate 2a with a yield of 64% and a purity of 98%.

(2) Preparation of Compound 2

45 g of sodium tetrakis(pentafluorophenyl) borate was dissolved in 100 mL of acetone, and 43 g of the intermediate 2a prepared in step (1) was then added. Stirring was performed at normal temperature until the intermediate 2a was dissolved. 200 mL of deionized water was then added to precipitate a white solid, suction filtration and recrystallization with methanol were performed to obtain 76 g of a solid. The solid was dried at 70° C. for 5 h to obtain the compound 2 with a yield of 90% and a purity of 98%.

MS(m/z): 687 (M+1)$^+$;

$^1$H-NMR (CDCl$_3$, 500 MHz): 0.9642 (6H, t), 1.1332-1.1932 (4H, m), 1.2911-1.3027 (4H, m), 1.8694-1.8663 (4H, m), 2.3433 (3H, s), 7.3281-8.1477 (24H, m).

Example 3

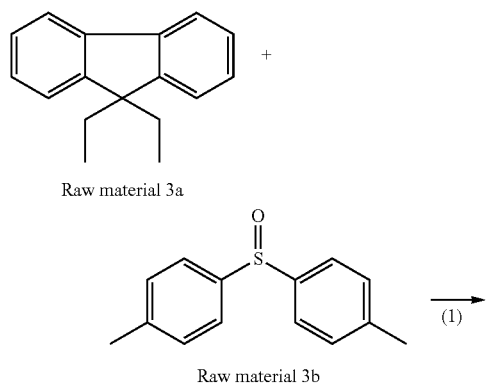

Raw material 3a

Raw material 3b

Intermediate 3a

Compound 3

(1) Preparation of Intermediate 3a 22 g of a raw material 3a, 28 g of aluminum trichloride, and 50 mL of dichloromethane were added to a 500 mL four-neck flask, and the temperature was reduced to 0° C. by an ice water bath. 46 g of a raw material 3b was dissolved in 100 mL of dichloromethane to form a mixed solution. The mixed solution was subsequently charged into a dropping funnel, and the temperature was controlled at 10° C. or less. This mixed solution was dropped in the four-neck flask within about 2 h. Stirring was continued for 24 h after completion of dropping, and liquid phase tracking was performed until the raw materials did not change any longer. The materials were then slowly poured into 200 g of deionized water with stirring to precipitate a solid, and suction filtration was performed to obtain a light yellow solid. This light yellow solid was dried in an oven at 80° C. for 2 h to obtain 56 g of the intermediate 3a with a yield of 65% and a purity of 98%.

(2) Preparation of Compound 3

60 g of Sodium Perfluorobutylsulfonate was Dissolved in 100 mL of Acetone, and 55 g of the intermediate 3a prepared in step (1) was then added. Stirring was performed at normal temperature until the intermediate 3a was dissolved. 200 mL of deionized water was then added to precipitate a white solid, suction filtration and recrystallization with methanol were performed to obtain 88 g of a solid. The solid was dried at 70° C. for 5 h to obtain the compound 3 with a yield of 90% and a purity of 98%.

MS(m/z): 650 (M+1)$^+$;

$^1$H-NMR (CDCl$_3$, 500 MHz): 0.9444-0.9601 (6H t), 1.9086-1.9146 (4H, m), 2.3607 (12H, s), 7.1061-7.7677 (22H, m).

Examples 4-18

Compounds 4-18 as shown in Table 1 below were synthesized by using corresponding raw materials with reference to the methods of Examples 1-3. The structures of compounds of interest and mass spectrometry data thereof were listed in Table 1.

TABLE 1

| Example | Compound | MS (m/z) |
|---|---|---|
| Example 4 | 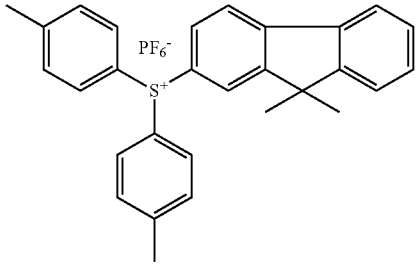<br>Compound 4 | 408 |
| Example 5 | 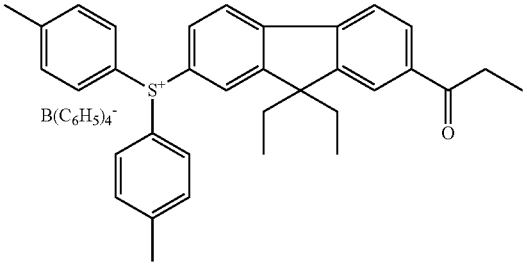<br>Compound 5 | 492 |
| Example 6 | 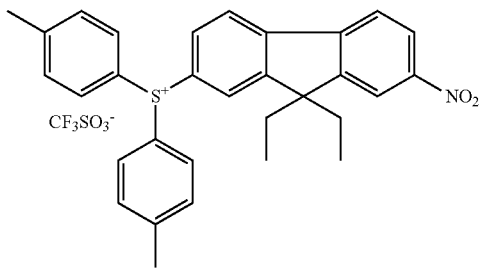<br>Compound 6 | 481 |
| Example 7 | 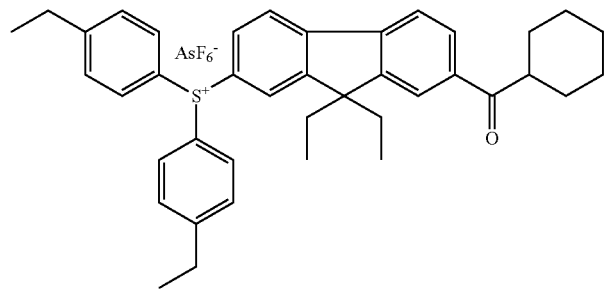<br>Compound 7 | 574 |

TABLE 1-continued
| Example | Compound | MS (m/z) |
|---|---|---|
| Example 8 | 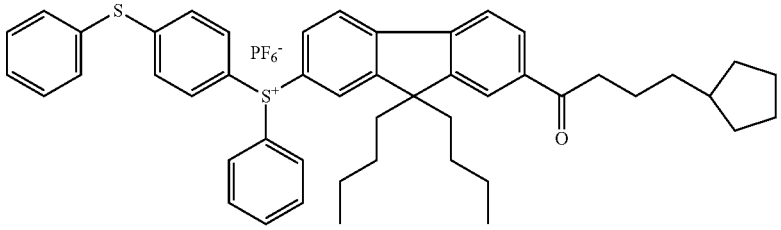<br>Compound 8 | 711 |
| Example 9 | 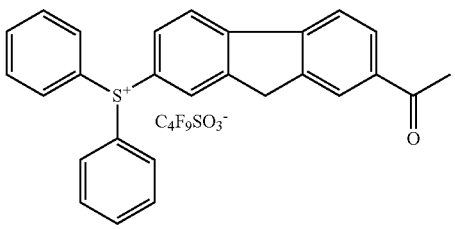<br>Compound 9 | 394 |
| Example 10 | 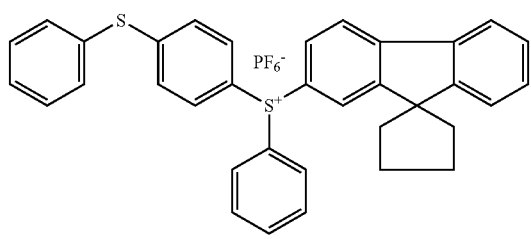<br>Compound 10 | 514 |
| Example 11 | 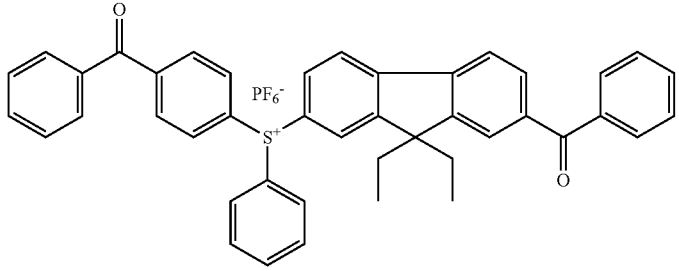<br>Compound 11 | 616 |
| Example 12 | 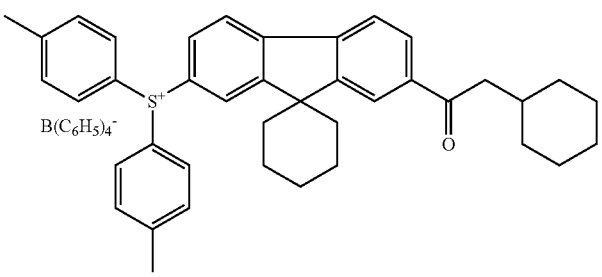<br>Compound 12 | 572 |

TABLE 1-continued

| Example | Compound | MS (m/z) |
|---|---|---|
| Example 13 | Compound 13 | 572 |
| Example 14 | Compound 14 | 586 |
| Example 15 | Compound 15 | 588 |
| Example 16 | Compound 16 | 650 |
| Example 17 | Compound 17 | 496 |

TABLE 1-continued

| Example | Compound | MS (m/z) |
|---|---|---|
| Example 18 | 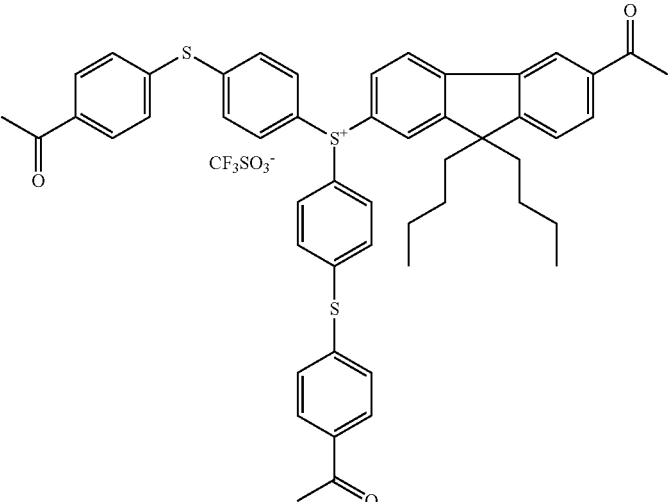  Compound 18 | 807 |

Evaluation of Properties

By formulating exemplary photocurable compositions, various application properties of the photoinitiator represented by formula (I) of this invention were evaluated, including aspects of photosensitive property, storage stability, mobility, yellowing resistance, and the like.

1. Formulation of Photocurable Compositions

Photocurable compositions were formulated according to the formulations as shown in Table 2. A cationic photoinitiator was first dissolved in a solvent, which was propylene carbonate, and then evenly mixed with a cation polymerizable monomer to obtain a photocurable composition by formulation.

Here, the cation polymerizable monomer was one or a combination of two or more of A1, A2, and A3:

A1: 3',4'-epoxycyclohexylmethyl 3,4-epoxycyclohexyl carboxylate (CAS: 2386-87-0);

A2: bis(3,4-epoxycyclohexylmethyl) adipate (CAS: 3130-19-6);

A3: 1,4-cyclohexanedimethanol divinyl ether (CAS: 17351-75-6).

The cationic photoinitiator was the cationic photoinitiator of this invention or a compound A and/or B as comparison.

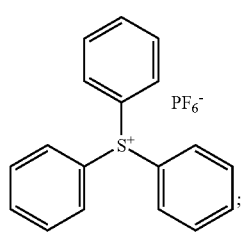

Compound A

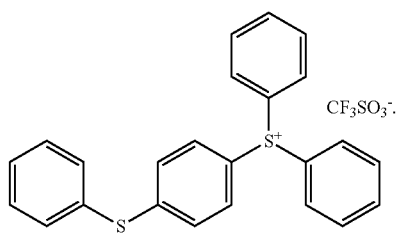

Compound B

The usage amounts of the components in Table 2 were all parts by mass.

TABLE 2

| Example/Comparative Example | Type, usage amount of photoinitiator | Solvent | A1 | A2 | A3 |
|---|---|---|---|---|---|
| Example 19 | Compound 1, 1 | 1 | 98 | | |
| Example 20 | Compound 1, 1 | 1 | | 98 | |
| Example 21 | Compound 2, 1 | 1 | 98 | | |
| Example 22 | Compound 2, 1 | 1 | | | 98 |
| Example 23 | Compound 3, 1 | 1 | 98 | | |
| Example 24 | Compound 3, 1 | 1 | 50 | 48 | |
| Example 25 | Compound 10, 1 | 1 | | 98 | |
| Example 26 | Compound 15, 1 | 1 | | 98 | |
| Example 27 | Compound 16, 1 | 1 | | | 98 |
| Example 28 | Compound 17, 1 | 1 | 50 | 48 | |
| Example 29 | Compound 18, 1 | 1 | | 50 | 48 |
| Comparative Example 1 | Compound A, 1 | 1 | 98 | | |
| Comparative Example 2 | Compound A, 1 | 1 | | 98 | |
| Comparative Example 3 | Compound B, 1 | 1 | | 98 | |
| Comparative Example 4 | Compound B, 1 | 1 | | | 98 |
| Comparative Example 5 | Compound B, 1 | 1 | 50 | 48 | |

2. Test of Photosensitive Property

The composition described above was stirred under a yellow light lamp. Materials were taken on a PET template and roll coating was performed to form a film, and the solvent was removed by drying at 90° C. for 5 min, to form a coating film with a film thickness of about 2 μm. A substrate formed with the coating film was cooled to room temperature, and the coating film was exposed with an exposure time of 2 s by irradiating with a high-pressure mercury lamp (exposure machine model: RW-UV70201, wavelength: 200-500 nm, light intensity: 100 mW/cm$^2$) and placed at room temperature for 2 min to observe the pencil hardness of a cured film thereof (the test method was referred to GB/T 6739-1986). A higher pencil hardness indicated a better photocurability of a composition, that is, the sensitivity of the initiator was more excellent.

The evaluation was performed according to the criteria described below.
- ⊚: The pencil hardness was 2H or more.
- ○: The pencil hardness was H-2B.
- ●: The pencil hardness was 2B or less or its pencil hardness could not be measured.

3. Evaluation of Mobility

The composition described above was stirred under a yellow light lamp. Materials were taken on a PET template and roll coating was performed to form a film, the solvent was removed by drying at 90° C. for 5 min, to form a coating film with a film thickness of about 2 μm. A substrate formed with the coating film was cooled to room temperature, and the coating film was exposed with an exposure time of 4 s by irradiating with a high-pressure mercury lamp (exposure machine model: RW-UV70201, wavelength: 200-500 nm, light intensity: 100 mW/cm$^2$) to obtain a desired cured film. Next, 10 mL of methanol was used as a simulation liquid, and the cured film was placed in the simulation liquid and placed at room temperature for 24 h. The amount of the precipitated photoinitiator was analyzed with HPLC (LC-MS2020, Shimadzu, mobile phase: methanol/water=55/45, 0.5% dihydrogen phosphate salt). Content percentages of peaks in the liquid phase were used for comparison. The lower the relative content of the initiator in the liquid phase was, the less possibly the migration would occur.

The evaluation was performed according to the criteria described below.
- ⊚: The initiator was not detected.
- ●: The initiator was detected.

4. Evaluation of Yellowing Resistance

The composition described above was stirred under a yellow light lamp. Materials were taken on a PET template and roll coating was performed to form a film, the solvent was removed by drying at 90° C. for 5 min, to form a coating film with a film thickness of about 2 μm. A substrate formed with the coating film was cooled to room temperature, and the coating film was exposed with an exposure time of 4 s by irradiating with a high-pressure mercury lamp (exposure machine model: RW-UV70201, wavelength: 200-500 nm, light intensity: 100 mW/cm$^2$) to obtain a desired cured film.

Next, an RW-UV.2BP ultraviolet aging test tank was used for performing an aging test. The light source was a high-pressure mercury lamp (dominant wavelength: 365 nm, total power: about 2.2 KW). The cured film was continuously irradiated for 6 h, and the condition of yellowing of the cured film was observed:
- ⊚: It is colorless and transparent, and the surface was smooth.
- ○: It is yellowish, or the surface was sticky.
- ●: The surface yellowed and the viscosity increased.

5. Storage Stability

The photocurable composition obtained above was heated under protection from light in an oven at 80° C. for 24 h, and preserved under protection from light at normal temperature for 1 month. The viscosities of the composition before heating and after placing for 1 month were measured. A less increased viscosity indicated a better storage stability.

The evaluation was performed according to the criteria described below.
- ⊚: The change in the viscosity was less than 1.5 times.
- ○: The change in the viscosity was 1.5 times or more.

Evaluation results were seen in Table 3.

TABLE 3

| Examples/Comparative Examples | Photosensitive property | Mobility | Yellowing resistance | Storage stability |
|---|---|---|---|---|
| Example 19 | ⊚ | ⊚ | ⊚ | ⊚ |
| Example 20 | ⊚ | ⊚ | ⊚ | ⊚ |
| Example 21 | ⊚ | ⊚ | ⊚ | ⊚ |
| Example 22 | ⊚ | ⊚ | ⊚ | ⊚ |
| Example 23 | ⊚ | ⊚ | ⊚ | ⊚ |
| Example 24 | ⊚ | ⊚ | ⊚ | ⊚ |
| Example 25 | ⊚ | ⊚ | ⊚ | ⊚ |
| Example 26 | ⊚ | ⊚ | ⊚ | ⊚ |
| Example 27 | ⊚ | ⊚ | ⊚ | ⊚ |
| Example 28 | ⊚ | ⊚ | ⊚ | ⊚ |
| Example 29 | ⊚ | ⊚ | ⊚ | ⊚ |
| Comparative Example 1 | ● | ○ | ● | ○ |
| Comparative Example 2 | ● | ○ | ● | ○ |
| Comparative Example 3 | ○ | ○ | ○ | ○ |
| Comparative Example 4 | ○ | ○ | ○ | ○ |
| Comparative Example 5 | ○ | ○ | ○ | ○ |

As could be seen from the results in Table 3, compared to a conventional sulfonium salt photoinitiator (compounds A and B), the photocurable composition using the cationic photoinitiator of this invention has an outstanding photosensitive property, pencil hardnesses of cured films exceeding 2H, and has characteristics of no proneness to migration, better yellowing resistance, and better storage stability.

It is to be noted that with respect to each of the cationic photoinitiators used in Examples 19-29, the molecular weight is greater than that of the compound A or B, the molar amount is relatively small in the case of the same mass, and the pencil hardness is 2H or more. This further demonstrates the advantages of the photoinitiator of this invention in terms of the photosensitive property.

What is claimed is:

1. A cationic photoinitiator, wherein the cationic photoinitiator has a structure as represented by general formula (I):

$$(R_2)m^2 \underset{R_3 \quad R_4 \quad R_5}{\diagdown} \underset{}{\diagup} (R_1)m^1 \diagdown S^+ - R_7 \quad nX^- \diagup R_6 \tag{I}$$

wherein,
R$_1$ and R$_2$ each independently represent a halogen, OH, CN, NO$_2$, a C$_1$-C$_{20}$ linear or branched alkyl group, a C$_3$-C$_{20}$ cycloalkyl group, a C$_4$-C$_{20}$ cycloalkylalkyl group, a C$_4$-C$_{20}$ alkylcycloalkyl group, or a C$_6$-C$_{40}$ aryl or heteroaryl group, wherein —CH$_2$— may be optionally substituted with —O—, —S—, —NH—, —CO—, —COO—, or —OCO—;

$m^1$ and $m^2$ represent numbers of $R_1$ and $R_2$ respectively, and $m^1$ and $m^2$ are each independently an integer of 0, 1, 2 or 3;

$R_4$ and $R_5$ each independently hydrogen, a $C_1$-$C_8$ linear or branched alkyl group, a $C_3$-$C_6$ cycloalkyl group, or a $C_4$-$C_{10}$ cycloalkylalkyl group, wherein acyclic —$CH_2$— may be optionally substituted with —O—, —S—, —CO—, —COO—, or —OCO—; or optionally, $R_4$ and $R_5$ may be linked to each other, along with the carbon to which they are attached, to form a cycloalkyl group;

$R_6$ and $R_7$ may be the same or may be different, and each independently represent a phenyl group, a diphenyl sulfide group, a benzophenone group, a fluorenyl group, a diphenyl ether group, or a carbazolyl group, each of which may be optionally substituted with a halogen, CN, $NO_2$, or a $C_1$-$C_8$ alkyl group, and —$CH_2$— in the $C_1$-$C_8$ alkyl group may be optionally substituted with —O—, —S—, —CO—, —COO—, or —OCO—;

$R_3$ represents hydrogen, a halogen, CN, $NO_2$, $R_8$, —CO—$R_8$, or a $S^+(R_6)(R_7)$ group; $R_8$ represents a $C_1$-$C_{10}$ linear or branched alkyl group, a $C_3$-$C_{10}$ cycloalkyl group, a $C_4$-$C_{15}$ cycloalkylalkyl group, a $C_6$-$C_{20}$ aryl group, or a $C_7$-$C_{20}$ arylalkyl group, wherein the cycloalkyl structure and the aryl structure, may be optionally substituted with a $C_1$-$C_6$ alkyl group, and —$CH_2$— may be optionally substituted with —O—, —S—, —NH—, —CO—, —COO—, or —OCO—;

$X^-$ represents a non-nucleophilic anion; and n is 1 or 2.

2. The cationic photoinitiator according to claim 1, wherein $R_1$ and $R_2$ each independently represent a halogen, OH, CN, $NO_2$, a $C_1$-$C_{10}$ linear or branched alkyl group, a $C_3$-$C_{10}$ cycloalkyl group, a $C_4$-$C_{12}$ cycloalkylalkyl group, a $C_4$-$C_{12}$ alkylcycloalkyl group, or a $C_6$-$C_{20}$ aryl or heteroaryl group, wherein —$CH_2$— may be optionally substituted with —O—, —S—, —NH—, —CO—, —COO—, or —OCO—.

3. The cationic photoinitiator according to claim 1, wherein $m^1$ and $m^2$ are each independently an integer of 0, 1, or 2.

4. The cationic photoinitiator according to claim 1, wherein $R_6$ and $R_7$ each independently represent a phenyl group, a diphenyl sulfide group, a benzophenone group, a fluorenyl group, a diphenyl ether group, or a carbazolyl group, each of which may be optionally substituted with CN, $NO_2$, or a $C_1$-$C_4$ alkyl group, and —$CH_2$— in the $C_1$-$C_4$ alkyl group may be optionally substituted with —O—, —S—, —CO—, —COO—, or —OCO—.

5. The cationic photoinitiator according to claim 1, wherein $R_3$ represents hydrogen, a halogen, CN, $NO_2$, $R_8$, —CO—$R_8$, or a $S^+(R_6)(R_7)$ group; $R_8$ represents a $C_1$-$C_6$ linear or branched alkyl group, a $C_3$-$C_8$ cycloalkyl group, a $C_4$-$C_{10}$ cycloalkylalkyl group, a $C_6$-$C_{10}$ aryl group, or a $C_7$-$C_{12}$arylalkyl group, wherein the cycloalkyl structure and the aryl structure may be optionally substituted with a $C_1$-$C_4$ alkyl group, and acyclic —$CH_2$— may be optionally substituted with —O—, —S—, —NH—, —CO—, —COO—, or —OCO—.

6. The cationic photoinitiator according to claim 1, wherein when $R_3$ represents a $S^+(R_6)(R_7)$ group, $R_3$ is bilaterally symmetrical with a $S^+(R_6)(R_7)$ group on the other side.

7. The cationic photoinitiator according to claim 1, wherein $X^-$ is $C_mF_{2m+1}SO_3^-$, $BF_4^-$, $SbF_6^-$, $AsF_6^-$, $PF_6^-$, or $B(C_6Q_5)_4^-$, wherein Q represents hydrogen or a halogen, and m is an integer of 1-8.

8. The cationic photoinitiator according to claim 1, wherein a value of n is the same as a number of $S^+(R_6)(R_7)$ groups in the general formula (I).

9. A preparation method of the cationic photoinitiator of claim 1, wherein a reaction process flow used is as shown below:

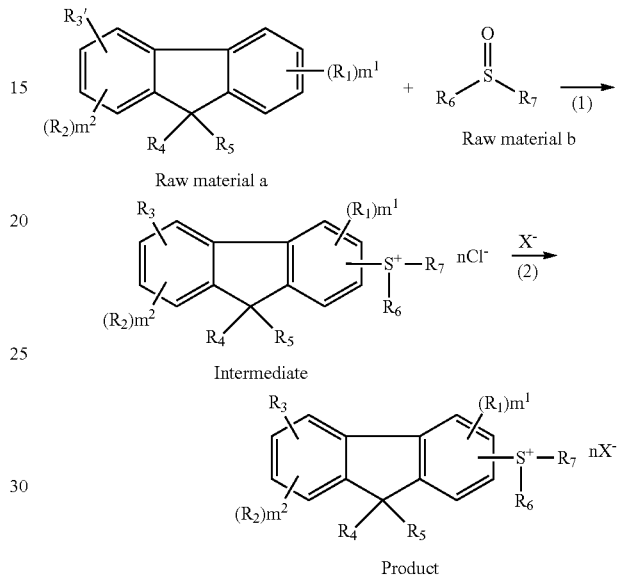

wherein $R_3'$ represents hydrogen when $R_3$ represents a $S^+(R_6)(R_7)$ group, and $R_3'$ represents $R_3$ in other occurrences;

the preparation method comprises:

(1) synthesis of the intermediate, wherein the raw material a and the raw material b are subjected to Friedel-Crafts reaction in an organic solvent under the action of aluminum trichloride or zinc chloride to synthesize the intermediate;

(2) synthesis of the product, wherein the intermediate is added to an organic solvent in which NaX or KX is dissolved and dissolved with stirring, deionized water is subsequently added with stirring to precipitate a solid, and suction filtration and recrystallization are performed to obtain the product; and X in the NaX and the KX represents a non-nucleophilic anion.

10. The cationic photoinitiator according to claim 1, wherein both $m^1$ and $m^2$ are 0.

11. The cationic photoinitiator according to claim 2, wherein both $m^1$ and $m^2$ are each independently an integer of 0, 1, or 2.

12. The cationic photoinitiator according to claim 2, wherein both $m^1$ and $m^2$ are 0.

13. The cationic photoinitiator according to claim 5, wherein when $R_3$ represents a $S^+(R_6)(R_7)$ group, $R_3$ is bilaterally symmetrical with a $S^+(R_6)(R_7)$ group on the other side.

* * * * *